(12) United States Patent
Wingate, III et al.

(10) Patent No.: US 12,059,386 B2
(45) Date of Patent: Aug. 13, 2024

(54) SMART PILL BOX

(71) Applicant: VIVA LIFE, INC., Lawrenceville, GA (US)

(72) Inventors: Harry L. Wingate, III, Statham, GA (US); William H. Wingate, Lawrenceville, GA (US); Joshua D. Wingate, Lawrenceville, GA (US)

(73) Assignee: VIVA LIFE, INC., Lawrenceville, GA (US)

( * ) Notice: Subject to any disclaimer, the term of this patent is extended or adjusted under 35 U.S.C. 154(b) by 0 days.

(21) Appl. No.: 18/384,319

(22) Filed: Oct. 26, 2023

(65) Prior Publication Data

US 2024/0074943 A1 Mar. 7, 2024

Related U.S. Application Data

(63) Continuation of application No. 18/074,505, filed on Dec. 4, 2022, now Pat. No. 11,890,258, which is a continuation of application No. 17/567,807, filed on Jan. 3, 2022, now Pat. No. 11,540,974, which is a continuation of application No. 17/060,029, filed on Sep. 30, 2020, now Pat. No. 11,241,360, which is a continuation of application No. 16/418,644, filed on May 21, 2019, now Pat. No. 10,842,712.

(51) Int. Cl.
| | |
|---|---|
| *A61J 1/03* | (2023.01) |
| *A61J 7/00* | (2006.01) |
| *B65D 85/00* | (2006.01) |
| *G16H 20/10* | (2018.01) |
| *H04W 4/80* | (2018.01) |

(52) U.S. Cl.
CPC ............... *A61J 1/03* (2013.01); *A61J 7/0084* (2013.01); *B65D 85/70* (2013.01); *G16H 20/10* (2018.01); *H04W 4/80* (2018.02)

(58) Field of Classification Search
CPC .......... A61J 1/03; A61J 7/0084; G16H 20/10; H04W 4/80; B65D 85/70
USPC ............... 340/540, 568.1, 571, 572.8, 572.1; 206/528, 538
See application file for complete search history.

(56) References Cited

U.S. PATENT DOCUMENTS

| | | | | |
|---|---|---|---|---|
| 2,167,926 A * | 8/1939 | Glasker | ................. | A45C 11/008 |
| | | | | 206/581 |
| 2,804,969 A * | 9/1957 | Barnett | ................. | A61B 50/312 |
| | | | | 206/229 |
| 4,429,793 A * | 2/1984 | Ehmann | ................. | A61M 5/003 |
| | | | | 62/457.2 |
| 5,579,916 A * | 12/1996 | Manko | .................. | A61F 15/001 |
| | | | | 206/440 |
| 6,935,133 B2 * | 8/2005 | Keeter | .................. | A61M 5/003 |
| | | | | 62/457.2 |

(Continued)

*Primary Examiner* — Jacob K Ackun
(74) *Attorney, Agent, or Firm* — Smith Tempel Blaha LLC; Gregory Scott Smith

(57) ABSTRACT

A device for organizing and tracking medication. The device includes compartments to contain medication, and each compartment includes an access door. A sensor element can detect if the device is moved, if the access door is opened and/or closed, and/or if medications have been placed into or removed from a compartment. A processor and/or external computing system provides alarms if medications is not properly taken, a filling service for stuffing the compartments and an administration service to verify the medications are properly taken.

20 Claims, 11 Drawing Sheets

(56) References Cited

U.S. PATENT DOCUMENTS

| | | | | |
|---|---|---|---|---|
| 7,565,979 B1* | 7/2009 | Gibson | A61J 7/04 | 206/363 |
| 8,006,846 B2* | 8/2011 | Robertson | A45C 13/02 | 206/479 |
| 8,085,135 B2* | 12/2011 | Cohen Alloro | A61J 7/0436 | 206/534 |
| D661,082 S* | 6/2012 | Wingate, III | A61J 1/03 | D3/203.3 |
| 10,842,712 B1 | 11/2020 | Wingate, III et al. | | |
| 11,241,360 B2 | 2/2022 | Wingate, III et al. | | |
| 11,540,974 B2 | 1/2023 | Wingate, III et al. | | |
| 2003/0042170 A1* | 3/2003 | Bolanos | B01L 1/52 | 206/569 |
| 2005/0029156 A1* | 2/2005 | Girzaitis | A61J 7/04 | 206/534 |
| 2007/0023318 A1* | 2/2007 | Mauk | B65D 83/0445 | 206/534 |
| 2008/0141700 A1* | 6/2008 | Fuchs | F25D 3/08 | 206/570 |
| 2009/0152159 A1* | 6/2009 | Beeman | A45C 11/00 | 206/459.1 |
| 2009/0267772 A1* | 10/2009 | Dehnadi | G07F 9/026 | 340/572.8 |
| 2011/0065732 A1* | 3/2011 | Jeannin | A61P 31/22 | 604/289 |
| 2014/0052467 A1* | 2/2014 | Maijala | G16H 20/13 | 206/534 |
| 2015/0366753 A1* | 12/2015 | Ryan | A61J 1/03 | 206/534 |
| 2016/0015602 A1* | 1/2016 | Panzini | A61J 7/0481 | 206/534 |
| 2016/0158108 A1* | 6/2016 | Gofer | A61J 1/03 | 206/539 |
| 2016/0158109 A1* | 6/2016 | Nova | A61J 7/0481 | 206/534 |
| 2023/0096507 A1 | 3/2023 | Wingate, III et al. | | |

* cited by examiner

SMART PILL BOX

BACKGROUND

According to the Institute of Medicine's Jul. 20, 2006 report bearing the title of PREVENTING MEDICATION ERRORS: QUALITY CHASM SERIES", it is estimated that in "any given week, four out of five adults in the United States will use prescription medicines, over-the-counter drugs, or dietary supplements of some sort, and nearly one-third of adults will take five or more different medications". "Statistics prove prescription drugs are 16,400% more deadly than terrorists". This was the title of an article published by Jessica Fraser on Jul. 5, 2005 on the NATRUALNEWS website which can be found at the URL of www<dot>naturalnews<dot>com. At the time the article was written, the author claimed that over 750,000 people die in the United States every year from conventional medicine mistakes with about 106,000 to 200,000 of these deaths being attributed to prescription drugs related issues. In the Institute of Medicine's Jul. 20, 2006 report, several reported statistics were provided with regards to adverse drug events (ADE) or injuries due to medication. For instance, between 380,000 to 450,000 ADEs were estimated to occur in hospitals but, the committed believed that these numbers were underestimates. The report stated that one study calculated that 800,000 preventable ADEs occure each yer in long-term care facilities while another that among outpatient Medicare patients, over 530,000 preventable ADEs occur per year. These statistics are exacerbated by our "take a pill to cure the ill" culture combined with the pharmaceutical ads that flood into our homes on prime-time TV.

An article by Michael A. Steinman, MD and Joseph T. Hanlon, PharmD, MS bearing the title MANAGING MEDICATIONS IN CLINICALLY COMPLEX ELDERS "THERE'S GOT TO BE A HAPPY MEDIUM" highlights the risks and issues involved in ADEs related to elderly patients having multiple medications. The article further addresses the issue by posing several needs in the art. First, a systematic approach to approaching prescribing is essential. Second, an essential first step is to know what the patient is taking right now, and to clarify what goals you are trying to achieve by prescribing drugs. Third, it is critical to individualize care based on what benefits and harms a patient is experiencing from their drugs.

"Medication Non-Compliance Estimated to Result in More Than 300,000 Deaths Each Year" was the title of an article posed by Kathy Wetters on Oct. 17, 2010 on the RIGHT AT HOME website. In this article, Ms. Wetters states "Medication non-compliance is becoming one of the most expensive and deadly problems in healthcare today. Hospital costs due to patient non-compliance are estimated at $8.5 billion annually. And with more than 300,000 deaths annually resulting from non-compliance, healthcare professionals, caregivers and Americans are left searching for new ways to fight this avoidable issue".

In an article published by FierceHealthcare bearing the title of PATIENTS NOT TAKING MEDICATIONS COST $300B, May 27, 2011 it is stated that the lack of prescription medication adherence costs between $250 and $300 billion annually. Supporting this position, the article cites a report from Express Scripts' released in April of 2011 determining that patients not taking their prescribed medications costs roughly $259 billion per year in emergency room and docober visits, as well as inpatient hospitalizations.

The website www<dot>abovetheinfluence<dot>com is a web campaign sponsored by the National Youth Anti-Drug Media Campaign and is directed to provide information about drug abuse, overdosing, and non-compliance. With regards to prescription drugs, ABOVETHEINFLUENCE writes:

"Prescription drugs are medicines that are prescribed to a patient by a doctor to manage pain, treat or cure a health condition such as pain, mental disease, diabetes, cancer, or common infections. These drugs are regulated by the Food and Drug Administration (FDA) and are shown to have medical benefits when prescribed and taken exactly as directed by a health provider. For people who are suffering, these drugs allow them to control their symptoms, cure or treat their diseases, control pain, or fight an infection. However, these medicines are only safe when taken exactly as directed by a doctor, healthcare provider, or as indicated on the packaging. This includes following directions on dosages, how often to take these drugs, and never taking any drug that is not prescribed for you."

"Taking prescription drugs that are not prescribed to you—or taking them in any way other than directed by a doctor—is considered non-medical use or abuse and can be as dangerous as taking an illegal drug, such as cocaine or heroin. "Misuse" of a prescription drug is taking it to treat a medical condition but not as directed by a doctor or packaging; "abuse" is taking prescription drugs with the sole intention of getting high. When misused or abused, many prescription drugs can be as dangerous and addictive as "street" drugs. In recent years, there has been a dramatic increase in the number of poisonings and even deaths associated with the abuse and misuse of prescription drugs, including prescription painkillers and anti-depressants." "In other words, even if a medication is prescribed to you, taking larger doses than prescribed, taking it more often than directed, or using it in a way that it is not intended, is abuse and can also lead to severe health consequences and addiction. Between 1995 and 2005, treatment admissions for dependence on prescription pain relievers such as oxycodone (OxyContin) and hydrocodone/acetaminophen (Vicodin) grew more than 300 percent."

"Taking prescription drugs without a prescription, not taking them as directed, or mixing them with alcohol are all unsafe and potentially deadly. A 2008 study based on 224,355 U.S. death certificates for which people died from medication errors showed that there was a 3,196 percent increase between 1983 and 2004 in deaths at home from combining prescription drugs with alcohol and/or street drugs."

"Additionally, getting prescription drugs without a prescription, called "diversion" is illegal and may put you at risk for arrest and prosecution. Regardless of how you acquire a prescription medication, using these types of drugs without a valid prescription—written for you—is unsafe and illegal."

The term "noncompliance" is used in medicine particularly in regard to a patient not taking a prescribed medication or following a prescribed course of therapy. For example, "As many as half of 'failures' of treatment to bring elevated blood pressure down to normal levels may be due to unrecognized lapses in taking antihypertensive drugs as prescribed, according to a new study by a team of researchers from the University of Lausannne, Switzerland." (Stephenson J, JAMA 282: 313, 1999)

Noncompliance may be overt (as with a Christian Scientist who rejects recommended therapy for religious reasons) or covert (as with children who are supposed to take an antibiotic, say they are taking it but are not, as revealed by a blood test to detect that antibiotic).

For some individuals, the number of medications that they must take can be overwhelming. Having multiple prescriptions with varying dosage schedules and amounts can become confusing. This, coupled by the similarity in the bottles and labeling, the non-descriptive naming conventions, busy schedules, etc., can easily lead to innocent mistakes by an individual that is taking the medicine—innocent mistakes that can be fatal.

Whether the cause of non-compliance is due to misuse, abuse, diversion or simply human error, it is clear that the problem is epidemic. Thus, there is a need in the art for a system to help reduce medicine non-compliance.

BRIEF SUMMARY

Various embodiments disclosed provide a tool, system, method and/or device to help organize and manage the storage, access and administration of prescription and/or over-the-counter medications. In general, a portfolio that includes various storage mechanism, holders and tools that can be used for managing a patient's medications. More specifically, in one embodiment, the portfolio is a two-sided brief-case like device that can be secured in a closed position, or opened to gain access to the interior of the portfolio. The portfolio may include multiple pockets on the outside for storing various items, and a variety of pockets, sleeves, receptors and Velcro or hook and loop structures for receiving and holding various elements such as a pill dispenser, containers, pill bottles, etc. In some embodiments, the portfolio is sold in a particular configuration and/or various versions may include different configurations. In other embodiments, the portfolio may be user configurable by including an interior that includes Velcro or hook and loop surfaces that can receive and securely hold various elements, such as medicine bottle receptors, pockets, sleeves, pill dispensers, communication devices, pouches, etc.

A particular embodiment includes a portfolio for holding medicine and medicine related items. The portfolio includes a first side and a second side. The first side is joined along one edge with the second side. The joint between the first and second side is flexible or hinged, thereby allowing the first side and the second side to be moved in a hinged like fashion away from each other to an open position and towards each other to a closed position. The one or more of the sides includes a plurality of receptors with each receptor configured to receive a pill bottle. One or more of the sides include at least one pocket for holding a notepad; a surface for receiving and holding pill dispenser; and a calendar. A latching mechanism may be included for securing the first side to the second side in the closed position.

In various embodiments, the first side and the second side may include interior surfaces with at least portions of the interior surfaces including a fastening element for receiving one or more elements. For instance, the fastening element may be Velcro, hook and loop, snaps, buttons, adhesive, loops, buttons, or other fasteners. The received one or more elements include a mating fastening element. For instance, if the fastening element is Velcro hooks, the mating fastening element may be Velcro loops, etc. As an example, the receptor strips may include the mating fastening element and can be secured to the interior surface of the first or second side. Further, one or more of the elements of a receptor strip, a pocket for holding a notepad; a pill dispenser; a note pad, a calendar, a pouch, a communication device, and a writing instrument may include a mating fastening element that can be secured to the interior surface of the first or second side.

In other embodiments, the plurality of receptor strips may be fixedly secured to the interior surface of the first or second side. Likewise, one or more of the elements of a receptor strip, a pocket for holding a notepad; a fastening element for a pill dispenser; a note pad holder, a calendar holder, a pouch holder, a communication device holder, and a writing instrument holder can be fixedly secured to the interior surface of the first or second side.

Further, in other embodiments, a combination of removably attached elements and fixedly attached elements may be utilized in the portfolio.

DETAILED DESCRIPTION OF EMBODIMENTS

The present disclosure presents a solution, in the form of an apparatus, a system and a method, to help reduce medicine non-compliance by introducing a single tool that alleviates many of the needs that are present in the art. The various embodiments operate to or provide solutions to assist in organizing the storage and dosing of medications. The various embodiments simplify, monitor, track and report the administration of medications. Thus, the various embodiments, as well as features and aspects thereof, are directed towards providing an organizer that can be used by individuals, caretakers, nurses, physician assistants, etc., in organizing, identifying and tracking the use, storage and dosing of prescription and over-the-counter medications.

The disclosed embodiments may include functional elements for the storage of prescription and over-the-counter medications (collectively referred to as medications) and a system and method for clearly labeling, organizing and monitoring access to and administration of the medications. In some embodiments, a dosage tracking functional element for sorting, tracking and verifying medication dosages may be included. Further, various embodiments may include additional functional elements such as but not limited to, one or more notepads for writing notes, cautions, instructions, questions/concerns, side effects, etc., to bring to the attention of the individual's physician, etc., a writing utensil storage element, a calendar, an electronic media and storage receptacle for the same that can contain further information such as instructions, warnings, etc., a calculator for converting measuring units, a dispenser for measuring dosages, and a cutter for splitting pills. In addition, the various embodiments may include sensors that can detect when certain of the medicine containers are being or have been accessed. Embodiments may also include a visual indication, such as LEDs of various colors that are used to communication information to the user, such as when medications are due to be administered, what and when medications were not delivered or accessed during a dosage window and preventive locks or measures to prevent early access to the medications (or return access when it is not remembered that a party has already taking the due dosage). The various embodiments may include a transceiver for communicating information to a central control system and or receiving information. The transceiver may also be used to sounding alarms, ordering additional supplies, requesting refiles of prescriptions, calling a doctor or calling 911. Embodiments may include a pulse ox to measure pulse rates and oxygen levels. Further, embodiments may include other sensors or tools for measuring other vital signs such as blood pressure, temperature, and sugar levels.

Turning now to the drawings in which like labels represent like elements, various embodiments of medication storage and organizer are presented.

Figure 1:
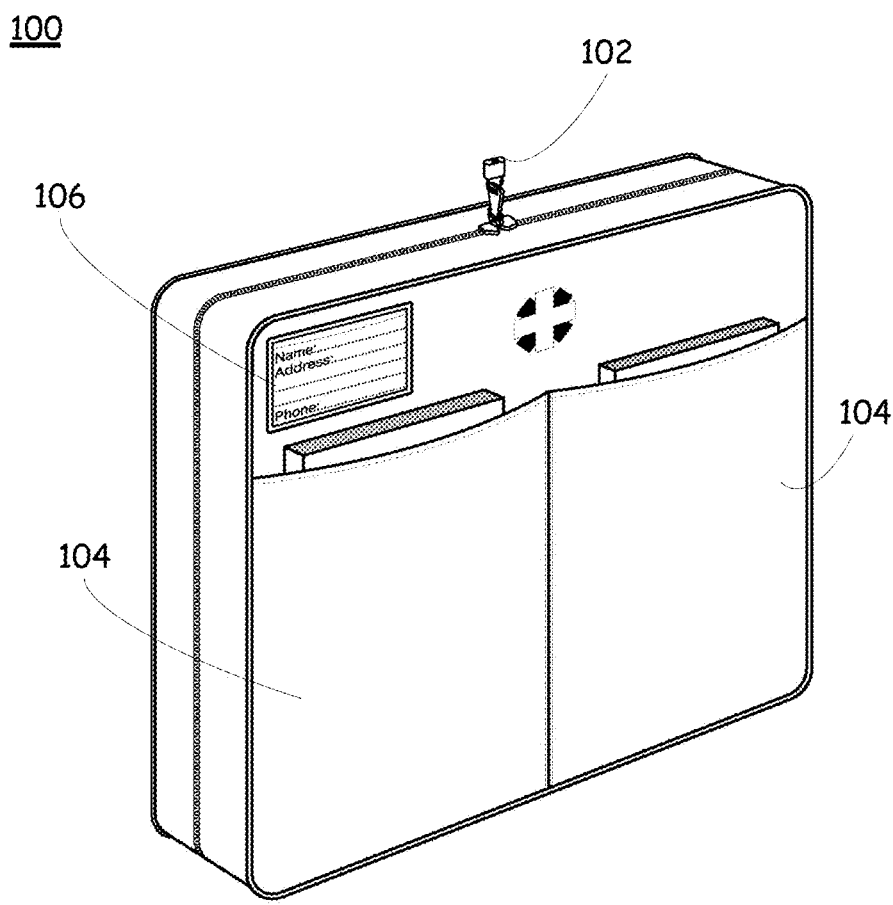
FIG. 1 is a perspective view of one embodiment of the medication storage and organizer in the form of a portfolio.

FIG. 1 is a perspective view of one embodiment of the medication storage and organizer in the form of a portfolio. The portfolio 100 is shown as including a closing mechanism 102 that can be actuated to securely close the portfolio or open the portfolio to allow access to the inside of the portfolio. The closing mechanism may be any of a variety of mechanisms and the illustrated embodiment presents the use of a zipper 102. It will be appreciated that the zipper 102 may include a locking mechanism to prevent unauthorized access. The locking mechanism can be a simple mechanical combination lock, a keyed lock, an electronic lock, etc. In other embodiments, the closing mechanism for the portfolio can use a variety of other techniques or mechanisms including but not limited to snaps, Velcro, straps, buckles, magnets, covering sleeve, or the like, as well as combinations of two or more of these techniques.

In the illustrated embodiment, the portfolio is shown as including two external pockets 104 and an identification tag 106. The external pockets 104 can be used for storage of a variety of items including as non-limiting examples, instructions, books, journals, insurance information, insurance cards, prescription cards, HMA cards, etc. Although only two external pockets are illustrated, it should be appreciated that more or fewer pockets can be used in various embodiments. The identification tag 106 allows for the ownership and contact information of the portfolio to be readily accessible and identified without having to gain access to the internal portions of the portfolio. In the illustrated embodiment, the identification tag 106 is shown as a card that can receive the owner's name, address and telephone number. However, it will be appreciated that additional or less information can also be provided. In addition, other forms of an identification tag may also be employed, such as an LED display, LCD display or other electronic or mechanical display.

Figure 2:
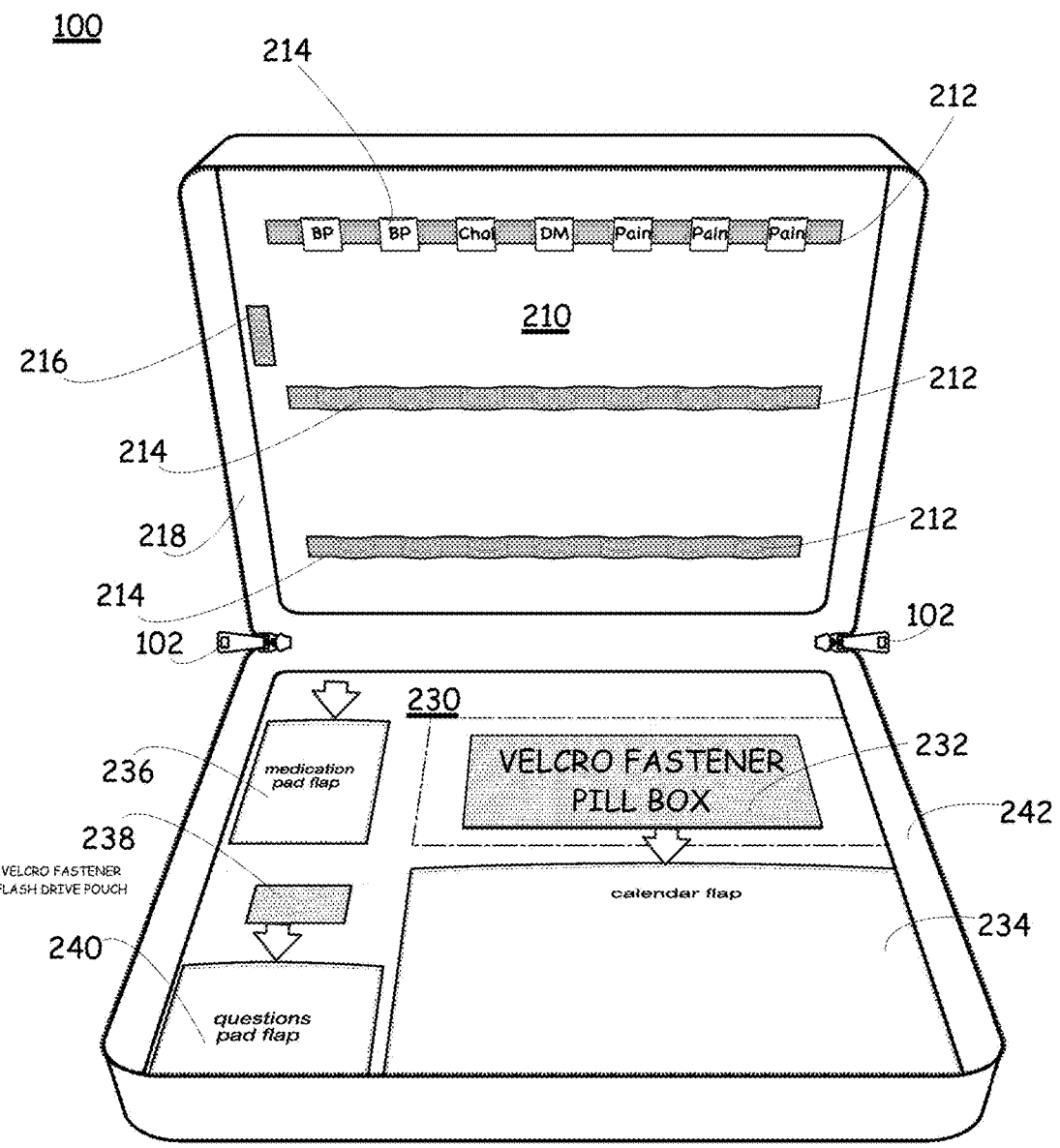
FIG. 2 is a perspective view of the inside of an exemplary embodiment of the portfolio.

FIG. 2 is a perspective view of the inside of an exemplary embodiment of the portfolio. The portfolio 100 is shown as including a top or back section 210, and a bottom or front section 230. The top section 210 is connected to the bottom section 230 along a single side using a flexible material or a hinge or a hinging structure. The connection between the top section 210 and the bottom section 230 enables the top section 210 to be moved away from the bottom section 230 into an opened position, or moved towards the bottom section 230 to a closed position. The top section 210 is shown as including multiple storage receptors 214 arranged in three receptor rows 212 of seven receptors 214 each. In addition, the illustrated embodiment includes a general receptor 216. The receptors 214 may be suitable for receiving and holding a standard pill bottle or other containers, such as medicine bottles, vitamin bottles, boxes of pills, etc. The illustrated receptors 214 are shown as being uniform in size and constructed using an elastic band that is tacked to the surface of the top section 210 at periodic intervals to form receptor loops for receiving the items, such as pill bottles. The receptor loops can be constructed at a single size that may accommodate small, medium and large pill bottles. However, in some embodiments, different loop sizes may be utilized and intermixed throughout the portfolio. For instance, some pill bottles may be extra large and require a larger receptor loop which would not be able to accommodate or securely hold smaller pill bottles. In addition, a variety of other mechanisms may be used for holding and securing the pill bottles, as well as other elements in the portfolio. For instance, a plurality of clips, similar to the clips used on the bottom of TV trays, microphone holding clips, etc. can be fixedly or removably attached to the interior surface of the portfolio. In such embodiments, the pill bottle can be pressed into or slid into the holding clip and secured in place. In addition, holders similar to those used for batteries can be used for receiving the pill bottles. Further, in some embodiments, the elastic strap 212 may include a plurality of snaps that snap to the surface of the back 210. The snaps may be spaces out such that a different number of snaps can be decoupled to accommodate different container sizes. For instance, one snap can be decoupled for small bottles, while 3 snaps may be decoupled for large bottles.

The general receptor 216 can be used for storage of a writing instrument, a tool such as a pill cutter, a dosage measuring device, or the like. It should be appreciated that the illustrated configuration is simply one of a variety of configurations that may be implemented in various embodiments. Some embodiments may use more or fewer medicine bottle receptors 214 and more or fewer general receptors 216.

The bottom section 230 is illustrated as including multiple regions for housing various functional components. In the illustrated embodiment, the bottom section 230 includes a Velcro fastener for a pill box 232, a pocket or flap for receiving a calendar 234, a pocket or flap for receiving a note pad 236, a Velcro fastener for receiving a detachable pouch or container 238, and a pocket or flap 240 for receiving and holding another note pad, a calculator, insurance card, etc.

The top section 210 and the bottom section 230 each are bordered by a flap 218 and 242 such that the flap of the top section 210 mates with the flap of the bottom section 230 to close the portfolio. As previously presented, the flaps may include a zipper 102 to secure the flaps together as well as other closing mechanisms. The flaps 218 and 242 can be constructed in a variety of manners. As non-limiting examples, the flaps may be (a) flexible to allow them to be pulled back over the top section 210 or bottom section 230 to aid in accessing the portfolio contents or (b) rigid to ensure protection of the portfolio contents and to help prevent items from falling out of an opened portfolio.

Figure 3:
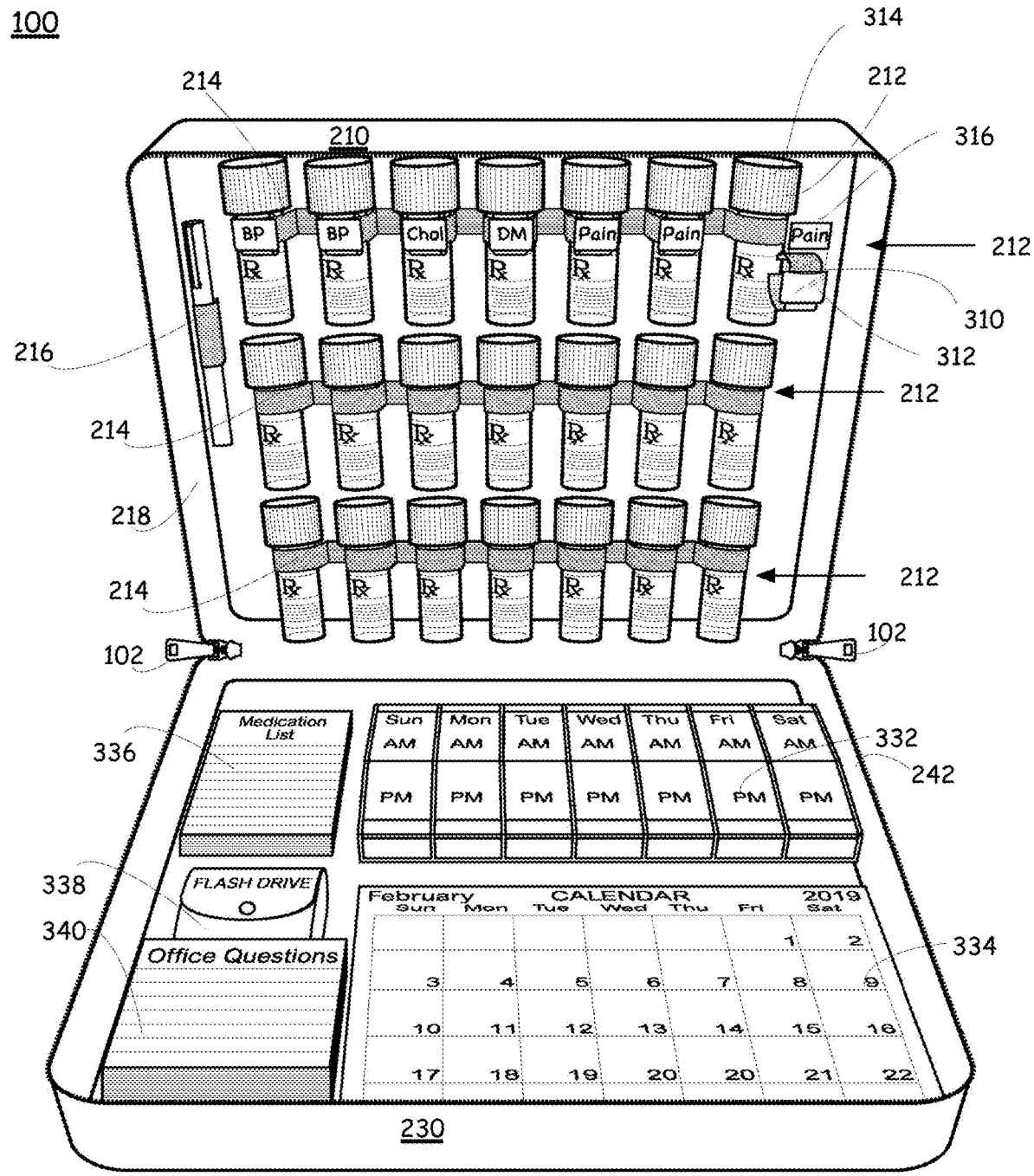
FIG. 3 is a perspective view of an open and populated portfolio in accordance with one embodiment.

FIG. 3 is a perspective view of an open and populated portfolio in accordance with one embodiment. The portfolio 100 is shown as including a top or back section 210, and a bottom or front section 230. The top section 210 is shown as including multiple storage receptors 214 arranged in three receptor rows 212 of seven receptors 214 each. Each of the receptors 214 is illustrated as being populated with a medicine bottle 314. In the illustrated embodiment, attachable labels are presented for identifying the type of medication that is stored in a particular receptor 214. In the illustrated embodiment, the label includes a Velcro strip 310 that can be looped through the receptor strap 214. The Velcro strip 310 includes a label holder 312 and a label 316 that can be placed into or onto the label holder 312. It should be appreciated that labels could be included using a variety of other techniques. A few non-limiting examples include a label with a clip, a label holder fixedly attached to the receptors 214, a dry-erase type material fixedly attached to the receptor 214 or above/below the receptor 214 in such a manner that the medicine bottle would not obstruct its view, labels that can be attached directly to the bottles (either the side, top or bottom), etc.

In addition, the illustrated embodiment includes one or more general receptors 216. In the illustrated embodiment, a pen is shown as being inserted into the general receptor 216. In other embodiments, various tools or other devices can also be accommodated. For instance, a general receptor could be used to hold a cellular telephone, a pager, a personal data assistant (PDA), a notebook computer, an iPad, and/or an emergency transmitter (such as the "I have fallen and I can't get up" medical alert device), measuring tool, pill cutter, etc.

The bottom section 230 is illustrated as housing a note pad for listing medication and/or instructions 336, a pocket or pouch 338 for holding a flash drive or memory device, a note pad 340 for writing questions to be asked during a next visit to the doctor or pharmacy, a pill dispenser box 332 including compartments for morning and evening of each day of the week and a calendar 334. In the illustrated embodiment, the two note pads 336 and 340 and the calendar 334 are held in pockets 236, 240 and 234 respectively (see FIG. 2). The pill dispenser 332 and the pouch 338 may be secured into position by including mating Velcro on the underside of the pill dispenser and pouch.

In should be appreciated that in varying embodiments, the elements may be permanently secured or detachable as described.

In another embodiment of the portfolio, the interior may be fully customizable. This can be accomplished using a variety of techniques. For instance, the entire interior surface may include a hook and loop fastening material. In such embodiments, a portfolio may be sold with a general set of attachments and other attachments or options can be purchased and added separately. For instance, various receptor rows 212 may be included with the portfolio with the underside of the receptor row including a mating hook and loop material. Advantageously, in such a configuration the user can include various rows for various needs. As an example, each receptor row 212 may include various receptor sizes. In some embodiments, each row may focus on a particular receptor size while in other embodiments, receptor rows may include a variety of different receptor sizes. Similarly, the portfolio may be sold with a variety of other elements/devices such as a calendar, a variety of notepads, one or more pockets of varying sizes, one or more pill dispensers, a calculator, etc.

Figure 4A:
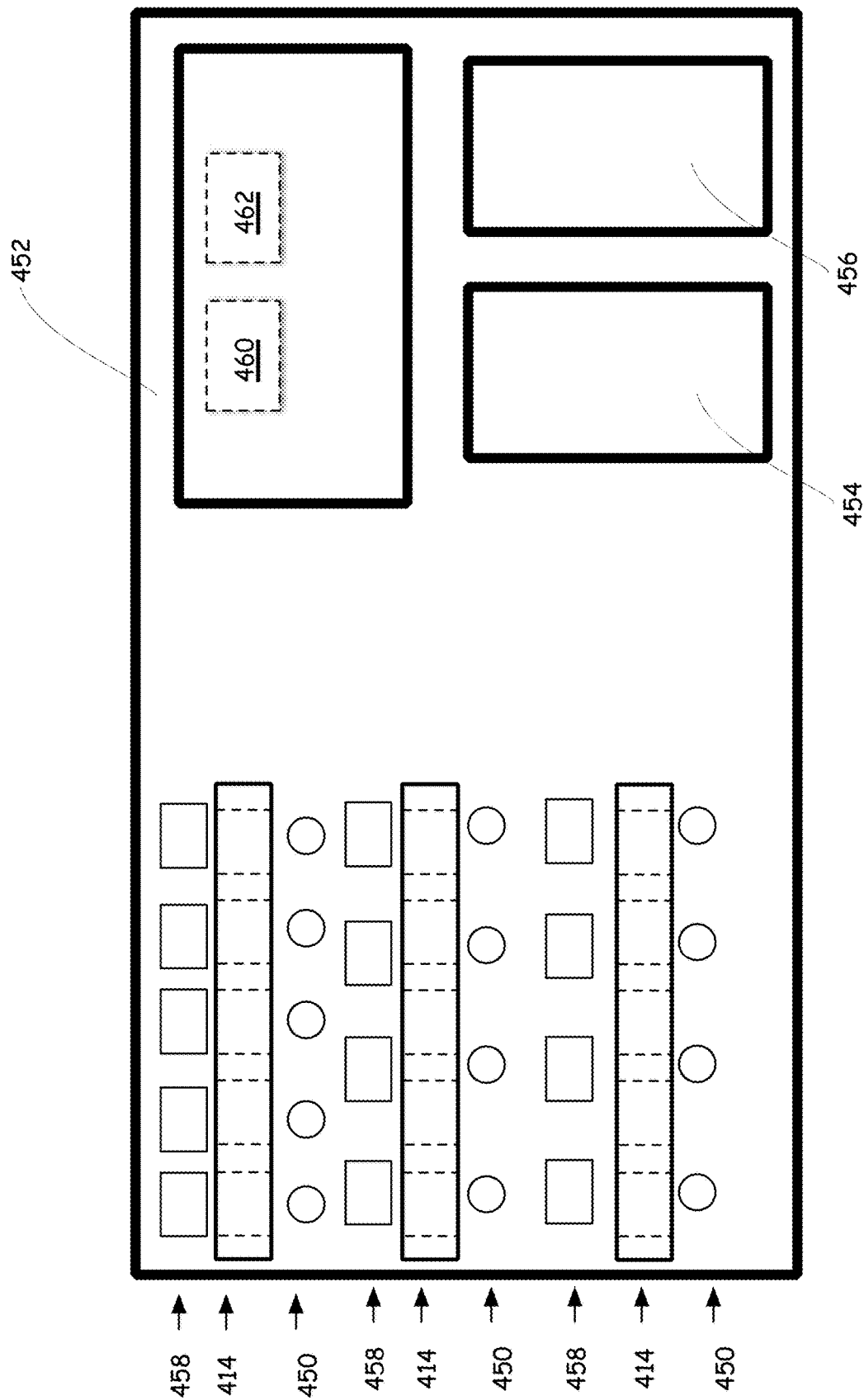
FIG. 4a is a conceptual diagram of a portfolio that is constructed in a side by side.

FIG. 4a-4d illustrate alternative configurations for various embodiments of the medicine portfolio and also illustrate additional features that may be incorporated into various embodiments. In FIG. 4a, the illustrated embodiment is a side by side configuration with three strips 414 of receptors positioned on the left side, and on the right side, a pouch 452, pad 454 and accessory 456. Each of the receptors 414 is illustrated as including a sensor 450 shown as being positioned slightly below the receptor 414. However, it should be appreciated that the sensor may also or alternatively be behind the receptor 414, above the receptor 414, in front of the receptor 414 or embedded within the strap of the receptor 414. The sensor 450 is configured to detect if and when a container has been removed from one of the receptacles. The sensors 450 may be any of a variety of sensors, including but not limited to, pressure sensors, light detectors, RFID sensors, push button switches, continuity detectors, etc.

The embodiment illustrated in FIG. 4a also includes a display device 458 associated with each receptor 414. The display device may be any of a wide variety of devices include one or more LEDs, an LED panel, LED segmented display, LCD panel, electroluminescence panel or any of a wide variety of displays that can present colors and/or text. In some embodiments, rather than a display, or in addition to a display, an audio interface may be included. The audio interface may include a single speaker that can be used to deliver audio signals indicative of a status, events, etc. Thus, the embodiments can be configured to be suitable for hearing impaired or visually impaired patrons.

The embodiment illustrated in FIG. 4a also includes a wireless transceiver 460. The transceiver may be Bluetooth, WiFi, unlicensed RF spectrum, cellular data, Infrared, or any of a wide variety of wireless technologies, either based on standards or proprietary. Preferably, the embodiments include BlueTooth technology to enable interfacing to a wide variety of devices. For instance, a smart phone could include a mobile app that is configured to control and monitor the portfolio. It should also be appreciated that the same functionality as described herein for wireless operation could also be obtained using wired technology. It should be appreciated that in some embodiments, a Bluetooth enabled pill box may also be utilized. The Bluetooth enabled pill box may utilize its own Bluetooth transceiver or it may simply interface to the processing unit 462 and utilize the same transceiver 460.

The embodiment illustrated in FIG. 4a is also shown with a processing unit 462. The processing unit may be as simple as an ASIC or programmable logic array that enables the state of each of the sensors 450 to be detected and transmitted by the transceiver 460 and to cause a status, alarm or instruction to be presented on the display and/or audio interface 458.

In a more complex embodiment, the processing unit may be a micro-controller that includes a firmware or software program. When executed, the program can operate to read and detect the current status of the sensors 450 and then to display the current status for each of the receptors 414 on the associated display device 458.

In an even more complex embodiment, the processing unit 462 may be partially or fully external to the portfolio. For instance, the processing unit may manage the interface through the transceiver 460 in communicating with an external device, such as a smart pad, a smart phone, a lap top computer, a notebook computer, a smart watch, a desktop computer, or the like. Alternatively, the transceiver 460 may be accessed and controlled directly by an external device and as such the processing unit 462 is fully external in such an embodiment.

In each of the embodiments that include a program, the program can be structured to perform a variety of tasks. Further, in some embodiments, a keyboard or input interface may be included to allow external programming or programming selection of the various features. Further, in embodiments that include at least a portion of the processing unit 462 as an external component, the external component may include a programming or program selection interface.

Reminder Service. One of the functions that can be provided in the various embodiments is a reminder service. For instance, the schedule for the administration of the medications can be programmed into the system with the schedule for each medication being entered. When the schedule reaches due time/date, the display device associated with the appropriate medication container can be set to indicate that it is time to take the medication. In one embodiment, the display may simply present a green light to indicate it is time to take the medication. In another embodiment, the display may indicate a counter that counts down to zero at the time the medication is to be administered. In another embodiment, the display may change colors and or flash to indicate it is time to take the medication. Further, in some embodiments the display may provide information such as the number of pills or the amount of the medication to take, the sequence to take the medication, indicate whether the medication should be taken with or without food, etc.

Verification Service. In certain embodiments, when a medication container is removed from the receptor 414 the sensor 450 associated with the receptor is triggered. This is an indication that the medication has been removed from the receptor 414 and the system my conclude that the medication has then been properly administered. However, it should be appreciated that in some embodiments, a smart container can be utilized to counter the number of pills or the size of the dosage that has been received.

Filling Instructions Service. In some embodiments, the portfolio includes a pill box. Pill boxes typically include compartments for holding various pills. The various compartments are typically organized into days of the week, such as 7 compartments (one for each day). Further, some pill boxes also include separate compartments for the morning (AM) and the evening (PM). Other embodiments may have more flexible labeling so that various periods for administration can be customized. The filling instruction service can be invoked manually or automatically in various embodiments and operates to instruct the user with regards to what medications and how much to obtain from the medication containers in the receptors 414 and where to place the medications in the pill box. For example, the program may begin by flashing the display 458 associated with a particular medication container. Once the medication container is removed from the receptor 414, the sensor 450 can detect this state change and the display device 458 can be updated to indicate the dosage to be placed in each container of the pill box. As a non-limiting example, the display may indicate that one pill should be placed the containers for each day of the week, or that X pills should be placed in the AM section for each day of the week. The pill box may include sensors to detect when each compartment is opened. Further, the pill box may include a sensor to detect the number of pills that have been placed into a container. This information can be relayed back to the processing unit and the display can be modified to confirm that the proper dosage was placed into the proper container. In some embodiments, the user may be prompted to verify that the dosage was entered into the proper box and then be required to actuate a button to confirm compliance. Other embodiments can include a variety of sensors and detectors to confirm that the proper dosage has been transferred into the proper compartment. This may include optical sensors, weight sensors, counters, etc. It is anticipated that the various embodiments would include specialized medicine containers that can be programmed to emit a proper dosage into a pill box container.

Automatic Refill Orders. In some embodiments, the various prescriptions can be monitored and the program this is aware of when the prescription needs to be refilled. Further, the program can access the Internet to identify lead times for ordering a refill to ensure that the refill orders are placed in time, thus maintaining continuity of administering the medications.

Interface to Physician/Pharmacy. In some embodiments, the physician or the pharmacy can actually send programming instructions to the portfolio whenever a prescription order is fulfilled. This information may include the amount of medication in the prescription, the timing of dosage of the medication and special instructions regarding the medication.

RFID Validation. When the medications are extracted from the receptors 414 and returned, it is possible that a user may get confused and place the medication containers into different receptors. The various embodiments may alleviate this issue in a couple of ways. One way is to use an RFID that is attached to the medication container. The programming can include an identification of which medication containers belong in which receptors 414. When the medication container is removed and then returned to the receptor 414, if it is not correct the receptor, the RFID can be actuated to verify if it is in the correct receptor. If the medication bottle is in the wrong receptor 414, an alarm can be sounded and a message can be presented to the user to indicate that the medication container is in the wrong receptor 414. For instance, the display in the incorrect receptor may flash red while the display device for the correct receptor may flash green as a non-limiting example. In another embodiment, when the RFID is detected for a medication container that has been placed in a receptor 414, rather than checking to verify that the medication container is in the correct receptor 414, the program may simply update the information to indicate the new location of that particular medication container. As such, all future status messages for that medication container will be sent to the new location.

The RFID validation may also be used to just detect when a medication container has been removed and returned to the receptor 414. As such, the RFID validation then becomes the sensor 450.

Electronic/Smart pill box. As previously described, the various embodiments may incorporate or utilize an electronic/smart pill box that may be wireless enables, such as with Bluetooth technology or some other wireless or wired technology. Similar to the receptors 414, the various containers in the pill box may include a sensor and/or a display or feedback mechanism (audio, mechanical, visual, etc.). Such devices can include features such as detecting when a compartment has been opened, highlighting a compartment that contains a dosage that has come due, locking a compartment until the dosage window is active, etc. A communication enabled smart pill box can be programmed from an app or a computer program or a user interface to provide the dosage timing, the amount of dosage, etc. In addition, the smart pill box can also report status to a smart phone or computer app, doctor, caretaker, etc. when medications have been taken and when the dosage window has closed without the medication being taken.

In other embodiments, a standard pill box can be converted to a smart pill box. One technique is to mount a translucent or transparent pill box over an array of LEDs. The LEDs can be used to signal various status. For instance, a green LED positioned under a pill compartment can be illuminated when the dosage window is active for the medications within that compartment. Likewise, if the dosage window has expired without confirmation that the medications were taken, a yellow LED can be illuminated under the compartment of interest. When a compartment is not associated with an open dosage window or an overdue dosage, a red LED can be illuminated under the compartment. In addition, an array of photovoltaic cells can be attached to the top access doors to each compartment. When the portfolio is opened, all of the photovoltaic cells will detect light. Then if one compartment is opened, the photovoltaic cell associated with that compartment will be covered, thus triggering that an opening event has occurred. The array of LEDs and photovoltaic cells (or other sensors) can be tied to the processing unit 462 for being controlled and/or providing status or trigger events.

Scan bar code or QR code. In some embodiments, the portfolio may include a code scanner, such as a bar code or QR code as non-limiting example. Further, the scanner may be implemented on a mobile smart phone or other device that is communicatively coupled to the portfolio and/or the processing unit. In operation, when a new medication container is being introduced to the portfolio, or a refill is being provided, the bar code or QR code, etc., can be scanned. The scanned code would include or provide access to obtain information regarding the dosage, the dosage timing, doctor contact information, special instructions, refill information, etc. This information can then be loaded into the portfolio. As a non-limiting example, the processing unit 462 may then identify an available receptor and illuminate the receptor so that the user knows where to store the medication container. The program may then also turn on an indication to let the user know that the containers of a pill box need to be populated with the newly introduced medication.

Figure 4B:
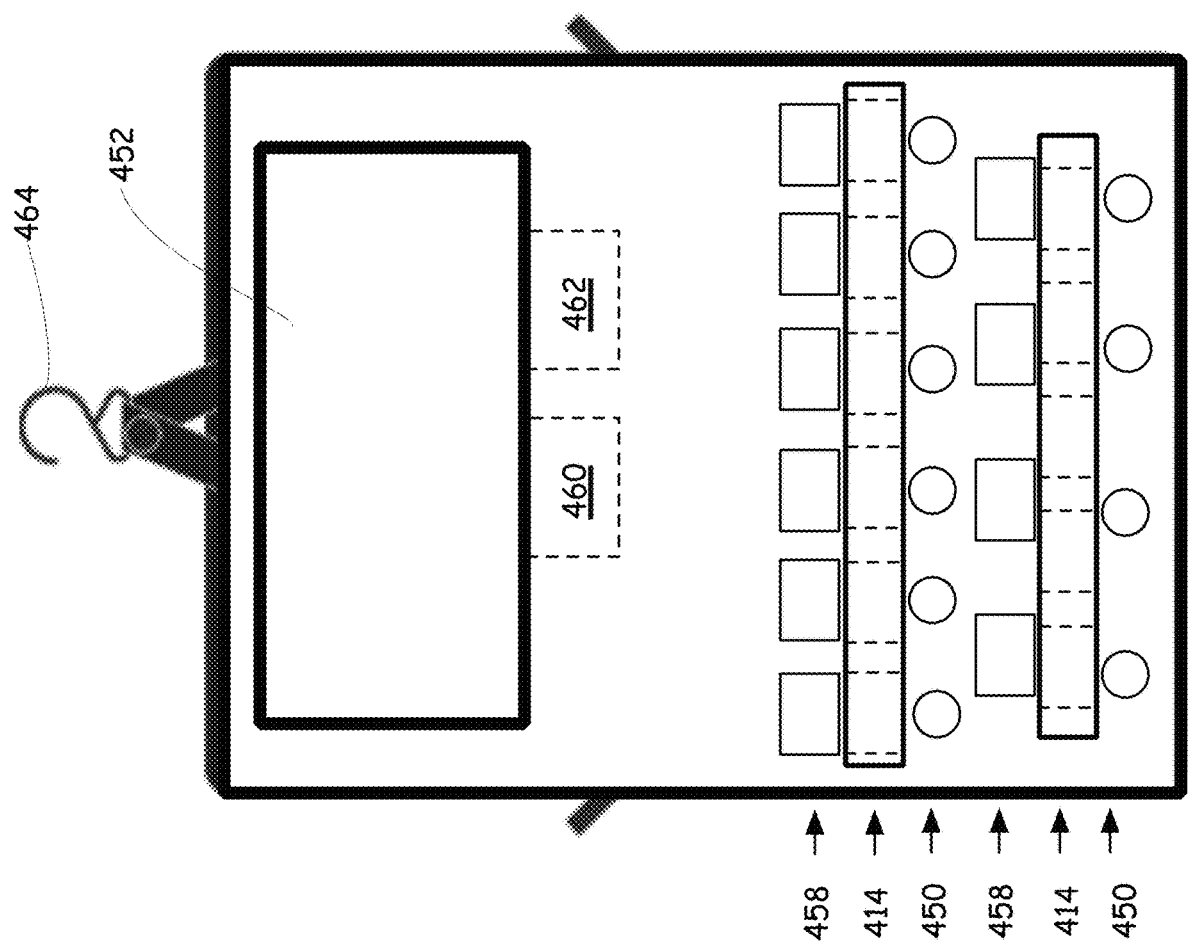
FIG. 4b is another embodiment that may include one or more of the afore-described features in the portfolio of FIG. 4a but includes an upper panel and a lower panel.

FIG. 4b is another embodiment that may include one or more of the afore-described features in a portfolio that includes an upper panel and a lower panel. In this embodiment, two rows of receptors 414 are illustrated with a row for 6 small medication containers and a row for 4 larger medication containers. A pouch 452 is provided and the portfolio can be conveniently hung with hook 464.

Figure 4C:
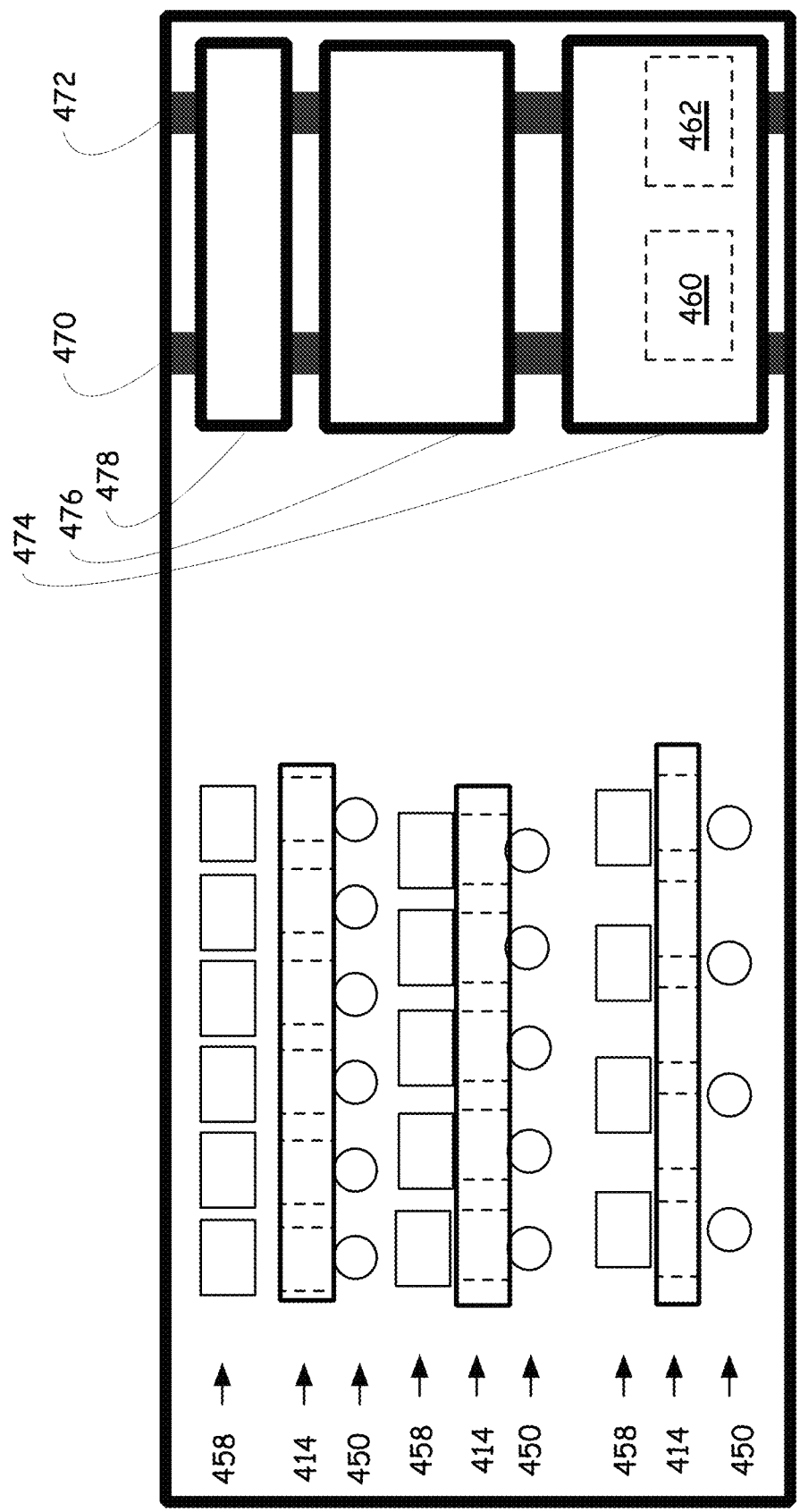
FIG. 4c is another embodiment that may include one or more of the afore-described features of the FIG. 4a portfolio but includes a left panel and a right panel.

FIG. 4c is another embodiment that may include one or more of the afore-described features in a portfolio that includes a left panel and a right panel. In this embodiment, two rows of receptors 414 are illustrated on the left panel, with a row for 6 small medication containers, a row for 5 mid-sized, and a row for 4 larger medication containers. Two VELCRO strips 470 and 472 are included on the outside of the right side panel and zipper pouches 474, 476 and 478 can be connected to the VELCRO strips.

Figure 4D:
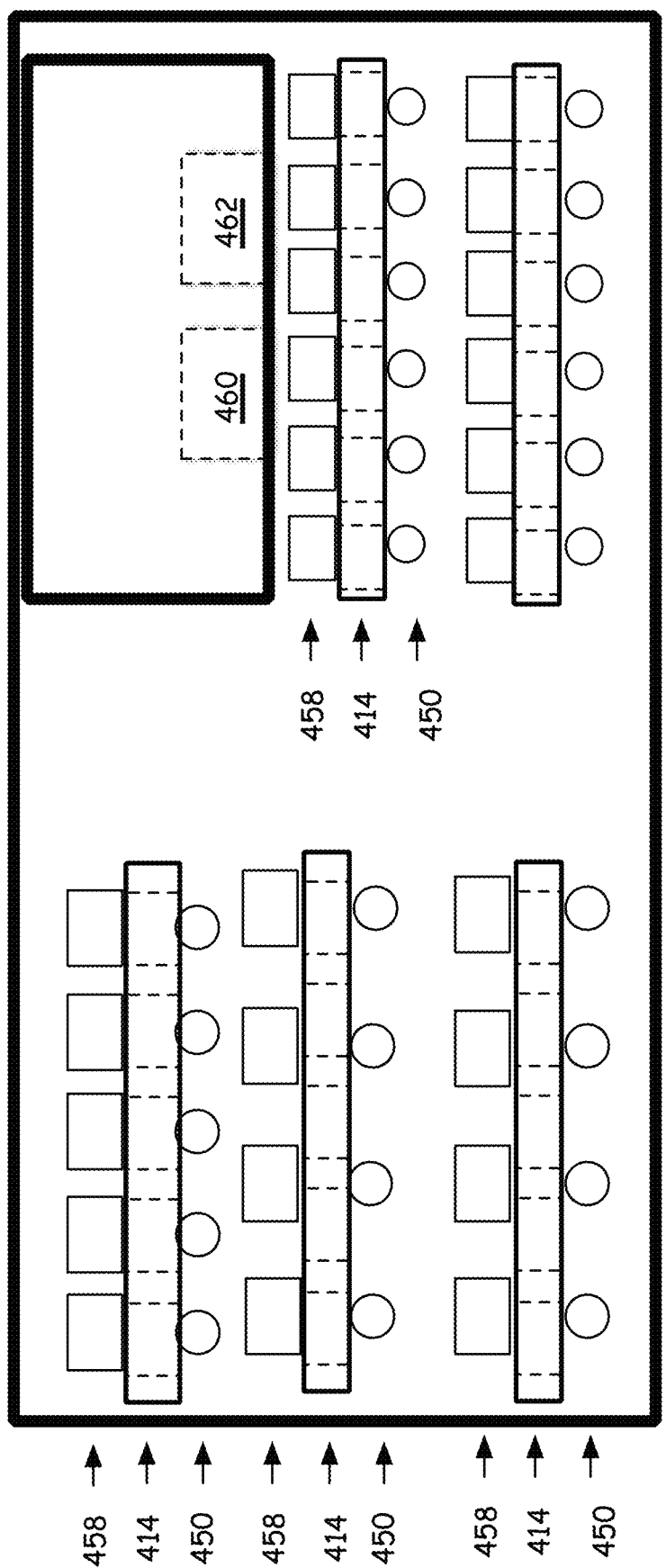
FIG. 4d is another embodiment that may include one or more of the afore-described features in a portfolio that includes a left panel and a right panel.

FIG. 4d is another embodiment that may include one or more of the afore-described features in a portfolio that includes a left panel and a right panel. In this embodiment, three rows of receptors 414 are illustrated on the left panel, with a row for 5 medium sized medication containers, two rows of 5 receptors for large medication containers and the right side includes two rows of small receptors for small medication containers.

Figure 5:
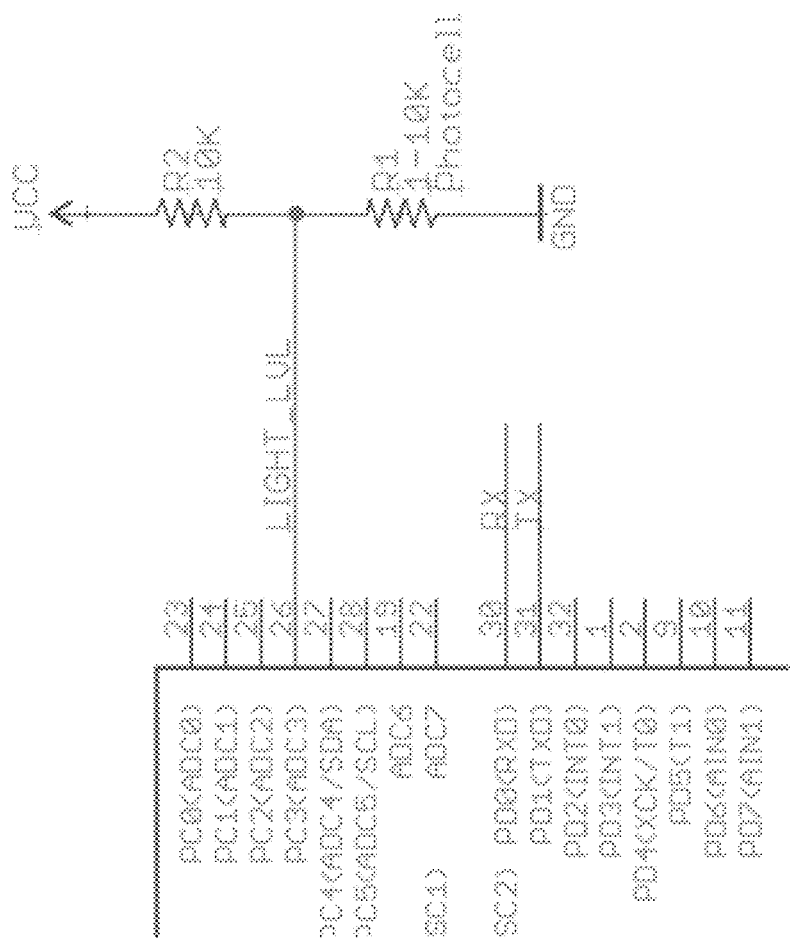
FIG. 5 is an example of how a photovoltaic device can be connected and used as a sensor in the various embodiments.

FIG. 5 is an example of how a photovoltaic device can be connected and used as a sensor in the various embodiments. The photovoltaic device R1 is connected in series with a resistor R2, wherein one end of the photovoltaic device R1 is connected to a first end of resistor R2 and the other end of the photovoltaic device R1 is connected to ground. The other end of resister R2 is connected to power VCC. The connection between resistor R2 and the photovoltaic cell R1 can be fed into an input of a microcontroller that can detect the value of the voltage being dropped across the photovoltaic cell. As such, when the photovoltaic cell is exposed to light, the resistance of R1 drastically changes, thus changing the value of the voltage drop across R1 and R2. When the photovoltaic cell is then shielded from the light, the resistance changes in the opposite direction and as such, so does the voltage drop across the photovoltaic device R1. As such, the micro-controller, by reading the voltage value at the connected port, can determine when the sensor is exposed or shielded from the light. and the series circuit is connected between power VCC and ground. The point of connection between the In other embodiments, rather than a folding portfolio, the portfolio may consist of a single tray and a sleeve that slides over the tray. In operation, the tray may be pulled or slid out of the sleeve to provide access to the interior of the portfolio. The sleeve can be open on two sides to allow the tray to be slid out in either direction or, the sleeve can include only a single opening on one side. In yet other embodiments the tray may include a top, similar to a cigar box, to allow access to the interior of the trey. In some embodiments, the portfolio may resemble a briefcase or a satchel with a carrying handle.

Figure 6:
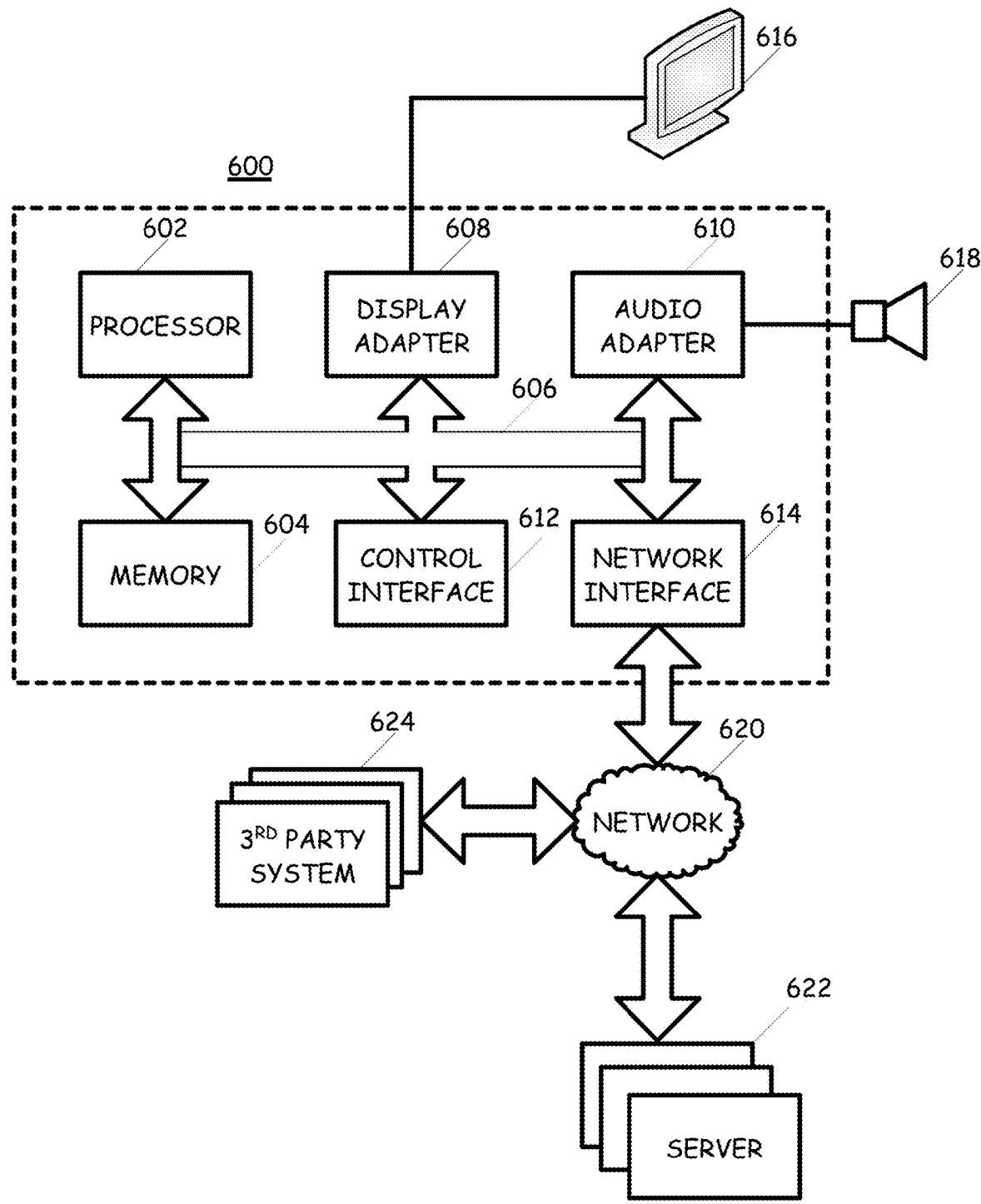
FIG. 6 is a functional block diagram of the components of an exemplary embodiment of the system or sub-system operating as a controller or processor in various embodiments.

FIG. 6 is a functional block diagram of the components of an exemplary embodiment of the system or sub-system operating as a controller or processor 600 that could be used in various embodiments of the disclosure for controlling aspects of the various embodiments, implementing functions or engines, implementing the GOG or components thereof. It will be appreciated that not all of the components illustrated in FIG. 6 are required in all embodiments of the GOG but each of the components are presented and described in conjunction with FIG. 6 to provide a complete and overall understanding of the components. Further, in some embodiments, additional components not illustrated may be added for particular interfaces and functionality. The controller can include a general computing platform 600 illustrated as including a processor/memory device 602/604 that may be integrated with each other or communicatively connected over a bus or similar interface 606. The processor 602 can be a variety of processor types including microprocessors, micro-controllers, programmable arrays, custom IC's, etc., and may also include single or multiple processors with or without accelerators or the like. The memory element 104 may include a variety of structures, including but not limited to RAM, ROM, magnetic media, optical media, bubble memory, FLASH memory, EPROM, EEPROM, etc. The processor 602, or other components in the controller may also provide functionalities such as a real-time clock, analog-to-digital convertors, digital-to-analog convertors, etc. The processor 602 also interfaces to a variety of elements including a control interface 612, a display adapter 608, an audio adapter 610, and network/device interface 614. The control interface 612 provides an interface to external controls, such as sensors, actuators, drawing heads, nozzles, cartridges, pressure actuators, leading mechanism, drums, step motors, a keyboard, a mouse, a pin pad, an audio activated device, as well as a variety of the many other available input and output devices or another computer or processing device or the like. The display adapter 108 can be used to drive a variety of user interface elements 616, such as display devices including an LED display, LCD display, one or more LEDs or other display devices. The audio adapter 610 interfaces to and drives another alert element 618, such as a speaker or speaker system, buzzer, bell, etc. and may also interface to an input device such as a microphone. The network/interface 614 may interface to a network 620 which may be any type of network including, but not limited to, the Internet, a global network, a wide area network, a local area network, a wired network, a wireless network, or any other network type including hybrids. Through the network 620, or even directly, the controller 600 can interface to other devices or computing platforms such as one or more servers 622 and/or third party systems 624. A battery or power source provides power for the controller 600.

Figure 7:
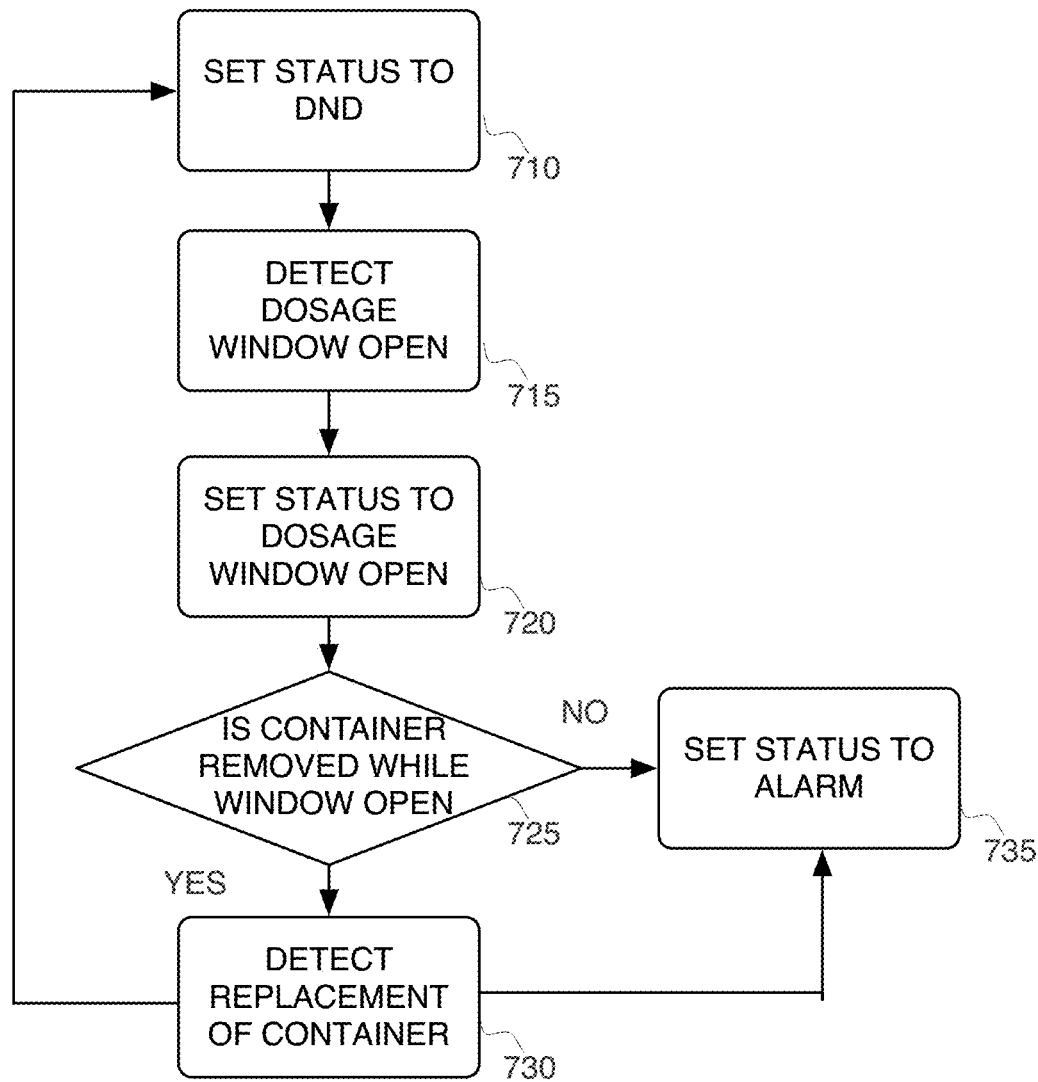
FIG. 7 is a flow diagram illustrating the operation of one function that may be made available in various embodiments.

FIG. 7 is a flow diagram illustrating the operation of one function that may be made available in various embodiments. In the illustrated diagram, the program 700 operates to set the status of the various display devices to a do not disturb state DND 710 to indicate that the medication should not be accessed at this particular time. When the processing unit determines that dosage window is open for one or more of the medication containers 715, the status indicator will be set to a dosage window open state 720. This status indicates to the user that the medication should be taken at this point. In some embodiments, an alarm may also be sounded.

If the processing unit detects that the medication container associated with a receptor that is in the dosage window open state 725, then the processing unit will begin to look for the container being placed back within the receptor 730. If the medication container is returned within a threshold period of time, processing returns to step 710 with the status set to the DND state. However, if the medication container is not replaced within the threshold period of time, an alarm state is entered 735. Similarly, if the medication container is not removed from the receptor during the dosage window, then an alarm is also sounded 735.

Figure 8:
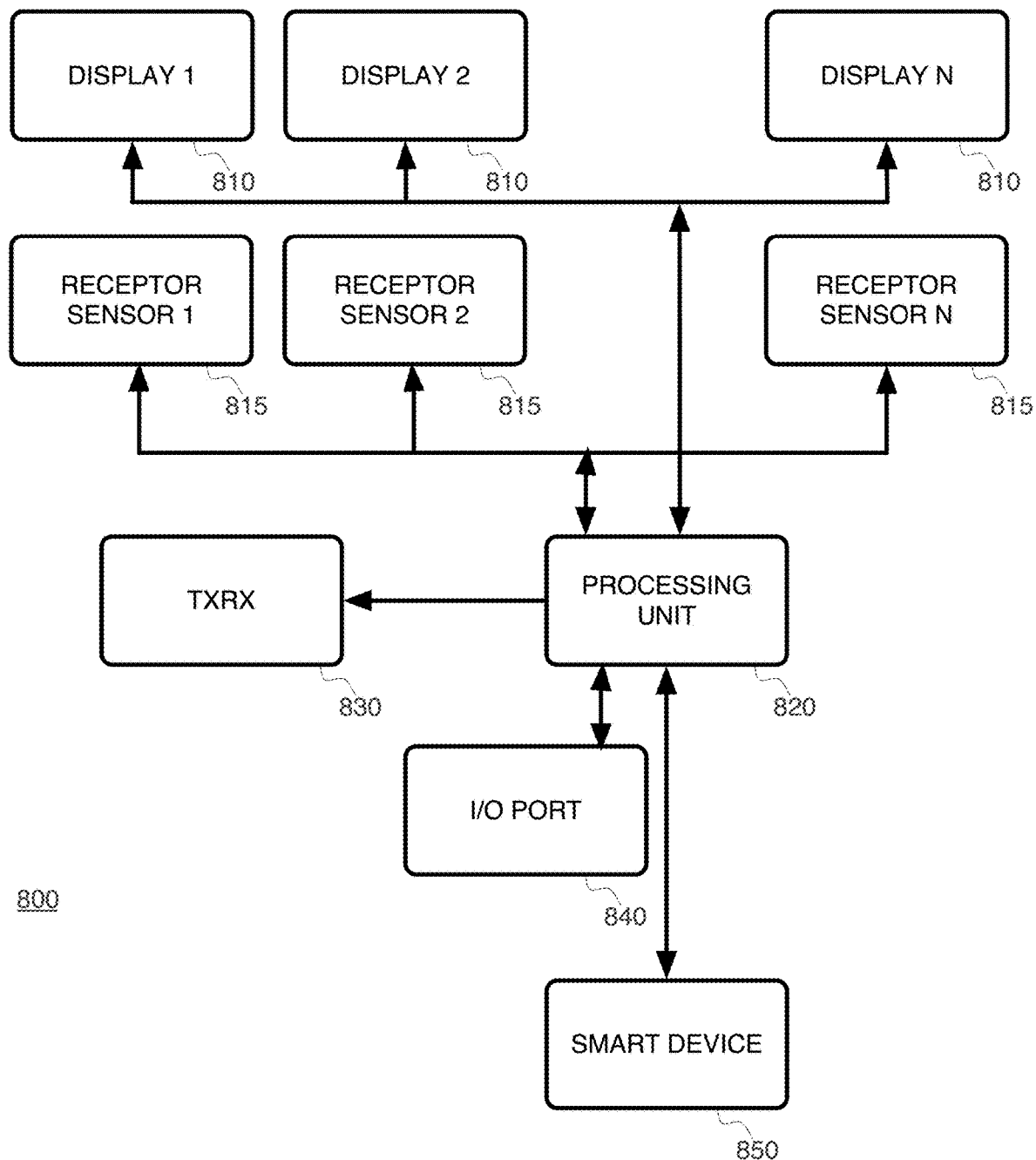
FIG. 8 is a block diagram illustrating functional blocks of an exemplary control structure that could be incorporated into one or more embodiments.

FIG. 8 is a block diagram illustrating functional blocks of an exemplary control structure that could be incorporated into one or more embodiments. The illustrated control structure 800 includes a processing unit 820. The processing unit interfaces to one or more receptor sensors 815 and one or more displays 810. The processing unit 820 can interface to the receptor sensors 815 to determine their current state, monitor changes in their state, enable or disable the sensor, enable or disable a lock on the receptor to allow or prevent extraction, and arm or disarm an alarm associated with the sensor. Further, the processing unit 820 can send control signals to the display devices 810. Depending on the structure of the display, the processing unit 820 can send varying levels of information. For instance, if the processing unit 820 senses that the displays 810 are of a certain type (i.e, LED, LCD, 7-segment display, multi-7-segment display, etc., the processing unit 820 can vary the types of control signals. If the display devices are a simple Boolean LED display, the processing unit 820 may simply turn the display device 810 associated with a particular receptor on when a dosage is due to be taken for the medications in that receptor as a non-limiting example. On the other hand, for a complex LCD display, the processing unit 820 could present a timer that counts down to the next dosage due time, display a picture of the pill shape and color to help prevent errors, and provide other messages such as "take this medicine with food", "do not drive for X hours after taking this medication", "do not take this medication with alcohol" as a few non-limiting examples. The display devices 810 can also be used as visual alarms. Further, the display devices 810 may also include an audible component such as a buzzer, an electric tone generator or even a speaker and the processing unit 820 can send message signals and/or alarms to the audible component as well. The processing unit 820 interfaces to the transceiver 830 to communicate with external devices, the user's smart phone or smart tablet, a control system at the pharmacy, doctor's office, etc. The processing unit 820 also interfaces to an I/O Port 840, such as a USB, FIRE, RS232 or any other of a wide variety of standard or proprietary ports/protocols. Similar to the transceiver 830, the I/O Port 840 can be used to obtain system status from the processing unit 820 or provide information and/or controls to the processing unit 820. For instance, a pharmacist can load an entire portfolio with medications and then transmit the control, alert, dosage, etc. information through the transceiver 830 and/or I/O Port 840. In addition, in some embodiments a keyboard and/or display can be attached to the I/O port 840 to conduct testing and maintenance on the system and/or to load or program control, alert, dosage, etc. information. The processing unit 820 can also interface to a smart device 850. The smart devices can be any of a wide variety of devices such as BlueTooth enable pill boxes, BlueTooth enable pill bottles, smart phones, smart tablets, health monitoring systems such as blood pressure, temperature, heartbeat, etc. systems.

In some embodiments, the portfolio may open as presented in FIGS. 1-3 and 4a-4c, but also include a quick access door located over the pill dispenser box to allow ease of access to the pill dispenser box. Similarly, the portfolio may include a drawer that can be pulled open to provide access to the pill dispenser or other elements in the portfolio without requiring the entire portfolio to be opened.

The portfolio can be constructed from a variety of materials. As non-limiting examples, the portfolio may be constructed of plastic, aluminum, silicone, cloth, GORE TEX, plastic with a cloth covering, as well as combinations or hybrids of any of these materials as well as other materials.

In some embodiments, the portfolio is constructed to be water proof or water resistant. In other embodiments, the portfolio is designed to easily slide into a refrigerator. In yet other embodiments, the portfolio may include one or more water proof pockets for holding BLUE ICE or similar devices that can be used to maintain the temperature within the portfolio at a particular temperature. In other embodiments, the portfolio may include insulation or a thermal protection. Alternatively, only portions, pockets, or sections of the portfolio may include insulation or thermal protection. Advantageously, such embodiments allow the portfolio to be portable even for medications that require refrigeration.

Some embodiments of the portfolio may include a pocket, sleeve or chamber for holding a thermos or water bottle.

In the description and claims of the present application, each of the verbs, "comprise", "include" and "have", and conjugates thereof, are used to indicate that the object or objects of the verb are not necessarily a complete listing of members, components, elements, or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. Further, the drawings and description has shown various elements being attached or affixed to certain areas and certain sides of the portfolio, but it should be appreciated that a variety of configurations may be employed such that any of the described elements can be placed at any location on any side of the portfolio's interior or exterior.

It will be appreciated by persons skilled in the art that the present invention is not limited by what has been particularly shown and described herein above. Rather the scope of the invention is defined by the claims that follow.

What is claimed is:

1. An apparatus for organizing and tracking medication schedules:
    a plurality of compartments, each of the plurality of compartments being configured to house one or more pills and including an access door;
    a plurality of sensor elements, each of the plurality of sensor elements associated with one of the plurality of access doors and identifies the access door being in an open state or a closed state;
    a memory element;
    a processor communicatively coupled to the sensor element and the memory element, and in response to instructions within the memory element, the processor is configured to:
        read a medication schedule from the memory element;
        monitor the plurality of sensor elements to record a current state and time/date of the plurality of access doors; and
        trigger an alarm if a particular access door was not opened during a particular window of time that a medication is due based on the medication schedule.

2. The apparatus of claim 1, further comprising an interface to a smart phone, and the processor is configured to trigger an alarm by sending a signal to the smart phone.

3. The apparatus of claim 1, further comprising a display device communicatively coupled to the processor, and the processor is configured to trigger an alarm by sending a signal to the display device.

4. The apparatus of claim 1, further comprising an interface coupled to the processor and the processor is configured to trigger an alarm by sending a signal to the interface.

5. The apparatus of claim 1, further comprising a display element coupled to the processor, and wherein in response to instructions within the memory element, the processor is further configured to:
    identify when a current time/date reaches a due time/date in the medication schedule;
    identify a particular compartment of the plurality of compartments associated with the due time/date;
    provide an indicator on the display element to indicate that the due time/date for the particular compartment has been reached.

6. The apparatus of claim 5, wherein the processor is further configured to:
    remove the indicator on the display element when the access door of the particular compartment transitions to the open state within a threshold period of time around the due time/date.

7. The apparatus of claim 1, wherein the sensor element can detect the opening and closing of the access doors for each of the plurality of compartments.

8. The apparatus of claim 7, wherein a filling instruction service interacts with the plurality of sensor elements to confirm that for a particular compartment of the plurality of compartments, the access door has been opened and closed, whereby indicating that the medication has been placed in the particular compartment.

9. The apparatus of claim 8, wherein the processor can detect placement of medication in each of the plurality of compartments.

10. The apparatus of claim 9, wherein the filling instruction service interacts with the plurality of sensor elements to confirm that for a particular compartment of the plurality of compartments, medication has been placed in the particular compartment.

11. The apparatus of claim 4, wherein the processor or an external computing system communicatively coupled to the processor is further configured to provide a medication administration service.

12. The apparatus of claim 11, wherein the provision of the medication administration service comprises providing a visual indicator to identify a particular compartment of the plurality of compartments that is to be accessed for the administration of a current dose.

13. The apparatus of claim 12, wherein the sensor element can detect the opening of the access doors for each of the plurality of compartments.

14. The apparatus of claim 13, wherein the medication administration service interacts with the sensor element to confirm that for the particular compartment of the plurality of compartments, the access door has been opened, whereby indicating that the medication has been removed from the particular compartment.

15. The apparatus of claim 12, wherein the sensor element can detect removal of medication from the particular compartment of the plurality of compartments.

16. The apparatus of claim 15, wherein the medication administration service interacts with the sensor element to confirm that for a particular compartment of the plurality of compartments, medication has been removed from the particular compartment.

17. The apparatus of claim 1, further comprising an interface to a smart phone, and the processor is configured to interface with the smart phone to:
    provide an indication of a trigger of the alarm;
    provide a filling instruction service; and
    provide a medication administration service.

18. The apparatus of claim 17, wherein the sensor element can detect the opening and closing of the access doors for each of the plurality of compartments.

19. The apparatus of claim 18, wherein the provision of the filling instruction service includes identifying medications and dosages to place in particular compartments of the plurality of compartments and interacting with the sensor element to confirm that for a particular compartment of the plurality of compartments, the access door has been opened and closed, whereby indicating that the medication has been placed in the particular compartment.

20. The apparatus of claim 19, wherein the provision of the medication administration service comprises providing a visual indicator to identify a particular compartment of the plurality of compartments that is to be accessed for the administration of a current dose and interacting with the sensor element to confirm that for the particular compartment of the plurality of compartments, the access door has been opened, whereby indicating that the medication has been removed from the particular compartment.

* * * * *